United States Patent
Lue

(10) Patent No.: US 9,925,225 B2
(45) Date of Patent: Mar. 27, 2018

(54) TREATMENT AND PROPHYLAXIS FOR GASTROESOPHAGEAL REFLUX DISEASE

(71) Applicant: NuBiome, Inc., Mountain View, CA (US)

(72) Inventor: Brian C. Lue, Mountain View, CA (US)

(73) Assignee: NuBiome, Inc., Mountain View, CA (US)

( * ) Notice: Subject to any disclaimer, the term of this patent is extended or adjusted under 35 U.S.C. 154(b) by 0 days.

(21) Appl. No.: 14/863,517

(22) Filed: Sep. 24, 2015

(65) Prior Publication Data

US 2016/0089405 A1    Mar. 31, 2016

Related U.S. Application Data

(60) Provisional application No. 62/056,323, filed on Sep. 26, 2014.

(51) Int. Cl.
*A61K 38/48*     (2006.01)
*A61K 35/747*    (2015.01)

(52) U.S. Cl.
CPC .......... *A61K 35/747* (2013.01); *A61K 38/482* (2013.01); *A61K 38/4886* (2013.01); *C12Y 304/21062* (2013.01); *C12Y 304/21026* (2013.01); *C12Y 304/24* (2013.01)

(58) Field of Classification Search
None
See application file for complete search history.

(56) References Cited

U.S. PATENT DOCUMENTS 7,901,925 B2 *   3/2011  Bojrab ................. A61K 35/747
                                                        424/93.45
2013/0302296 A1 * 11/2013  Lue ........................ A61K 35/74
                                                        424/93.44

FOREIGN PATENT DOCUMENTS

FR    WO 2013021239 A1 *  2/2013  ........... A23L 1/3014

OTHER PUBLICATIONS

Boyanova, L; et al; "Anti-Helicobacter pylori activity of *Lactobacillus delbrueckii* subsp. bulgaricus strains: preliminary report" Letters in Applied Microbiology, 48, 579-584, 2009.*
Pinchuk, Irina; et al; "In Vitro Anti-Helicobacter pyloriActivity of the Probiotic Strain Bacillus subtilis 3 Is Due to Secretion of Antibiotics" Microbial Agents and Chemotherapeutics, 45, 3146-3161, 2001.*
Yang et al. "Inflammation and intestinal metaplasia of the distal esophagus are associated with alterations in the microbiome" in Gastroenterology, Aug. 2009; 137(2):588-97.
Yang et al. "Molecular Pathways: Pathogenesis and Clinical Implications of Microbiome Alteration in Esophagitis and Barrett Esophagus" in Clinical Cancer Research, Feb. 2012; 18(8) 2138-44.

* cited by examiner

*Primary Examiner* — David W Berke-Schlessel
(74) *Attorney, Agent, or Firm* — Michael B. Einschlag

(57) ABSTRACT

An embodiment is a method of preventing, mitigating or treating Gastroesophageal Reflux Disease (GERD) that includes administering an effective amount of a medicament comprised of the *Lactobacillus bulgaricus* B-30892 strain and/or bioactive compounds from its supernatant to a human to prevent, mitigate or treat GERD.

5 Claims, No Drawings

TREATMENT AND PROPHYLAXIS FOR GASTROESOPHAGEAL REFLUX DISEASE

This patent application relates to U.S. Provisional Application No. 62/056,323 filed Sep. 26, 2014 from which priority is claimed under 35 USC § 119(e), and which provisional application is incorporated herein in its entirety.

BACKGROUND

Gastroesophageal Reflux Disease (GERD) affects many people around the world. Sometimes it is correlated with the presence, or after eradication, of *H. pylori* bacteria. Other times it is correlated with bouts of constipation. Researchers have also identified different mixtures of bacteria, more gram-negative, correlated with people with and without GERD, that colonize just above the stomach's sphincter valve that connects to the esophagus (see an article entitled "Inflammation and intestinal metaplasia of the distal esophagus are associated with alterations in the microbiome" by Yang et al in *Gastroenterology*, 2009 August; 137(2):588-97 and an article entitled "Molecular Pathways: Pathogenesis and Clinical Implications of Microbiome Alteration in Esophagitis and Barrett Esophagus" by Yang et al in *Clinical Cancer Research*, 2012 February; 18(8) 2138-44). GERD has long term consequences such as pain and inflammation that can cause esophageal cancer. Therefore, mitigating GERD can substantially improve a person's quality of life and lifespan.

Present treatments for GERD have primarily included proton-pump inhibitor drugs that reduce the strength of the secretion of stomach acid. Such drugs are prescribed because they increase the pH in the esophagus and reduce the pain and inflammation in the esophagus. Examples of such drugs are Omeprazol, Lansoprazole, Pantoprazole, Rabeprazole, and Ilaprazole. A problem with these approaches is that, since certain types of GERD are caused by a neurological disorder, the aforementioned drugs do not address the root cause of the problem, namely, a microbial agent or agents acting on the neuro-muscular system.

SUMMARY

One or more embodiments of the present invention address the root cause of the above-identified problem, namely, a neurological agent acting upon the nervous system controlling the gastrointestinal system (GI tract). In order to reduce neurological dysfunction of the GI tract, bacteria and/or enzymes that interfere with and/or reduce the neurological agents are used. It is believed that improperly behaving bacteria, or suboptimal populations of bacteria, create chemistries that cause GERD. In accordance with one or more embodiments, an effective amount of a medicament comprised of one or more suitable bacteria and/or a supernatant resulting from culturing the bacteria is administered to a person (or other mammal) to prevent, mitigate or treat GERD. An example of one suitable bacterium is, but is not limited to, *Lactobacillus bulgaricus* (formerly called *Lactobacillus delbrueckii* subsp. *bulgaricus*) B-30892. *Lactobacillus bulgaricus* B-30892 is commercially available from NuBiome, Inc. (Palo Alto, Calif.).

DETAILED DESCRIPTION

One or more embodiments of the present invention address a root cause of the above-identified problem, namely, a neurological chemical acting upon the nervous system of the GI tract. To reduce/neutralize activity of the neurological chemical thereto, in accordance with one or more of such embodiments, bacteria that interfere with and/or reduce the production and/or effects of the neurological chemical upon the nervous system are used. It is believed that microorganisms residing in the GI tract can create chemicals that affect portions of the nervous system and muscle tissues in the GI tract that control the sphincter valve at the entrance of the stomach from the esophagus.

In accordance with one or more embodiments, an effective amount of a medicament comprised of one or more suitable bacteria is administered to a person (or other mammal) to prevent, mitigate or treat GERD. An example of one such bacterium is, but is not limited to, *Lactobacillus bulgaricus* (formerly called *Lactobacillus delbrueckii* subsp. *bulgaricus*) B-30892 (*L. bulgaricus* B-30892). *L. bulgaricus* B-30892 is a non-pathogenic bacteria used to culture dairy products for human and mammalian consumption. *L. bulgaricus* B-30892 is commercially available from NuBiome, Inc of Palo Alto, Calif. An effective amount of *L. bulgaricus* B-30892 contained in the medicament is in a range from about $1 \times 10^5$ to about $1 \times 10^{12}$ colony forming units (CFU) of *L. bulgaricus* per day.

In accordance with one or more such embodiments, an effective amount of a medicament comprised of *Lactobacillus bulgaricus* bacteria and/or its supernatant (*L. bulgaricus* B-30892) is administered to a person (or other mammal) suffering from GERD. An effective amount of *L. bulgaricus* B-30892 contained in the medicament is in a range from about $1 \times 10^5$ to about $1 \times 10^{12}$ colony forming units (CFU) of *L. bulgaricus* B-30892 per day and/or supernatant resulting from culturing about $1 \times 10^5$ to about $1 \times 10^{12}$ colony forming units (CFU) of *L. bulgaricus* B-30892 per day.

In accordance with one or more further such embodiments, a medicament comprised: (a) of an effective amount of supernatant is administered to a human (or other mammal) to prevent/treat/cure GERD; and/or (b) of an effective amount of one or more bacteria capable of producing an effective amount of one or more enzymes is administered to a human (or other mammal) to prevent/treat/cure GERD. Further, in accordance with one or more further such embodiments: (a) an effective amount of the supernatant (for example, in sufficient volume) that is effective in destroying or deactivating neurological and/or muscular relevant chemicals that cause or exacerbate GERD; and/or (b) an effective amount of the one or more bacteria capable of producing one or more enzymes is an amount of the one or more bacteria (for example, in sufficient concentration) that is effective in producing an amount of the one or more enzymes effective in destroying or deactivating neurological agents, immunogens, mimics or antigens that cause or exacerbate GERD.

In accordance with one or more embodiments, an effective amount of oligopeptidase F (PepF) administered will depend upon the severity of the disease process (the PepF may be administered in one or more, preferably three, doses daily). However, an effective amount of PepF (for example, in sufficient concentration) is in a range from about 20 units/day to about 200 units/day, where the definition of a unit is an amount of PepF required to cleave one micromole of bradykinin at a pH of 8.0 and a temperature of 40° C.

In accordance with one or more further embodiments, an effective amount of PepF, in combination with the B-30892 strain, will be administered, and the amount will depend upon the severity of the disease process (the PepF and B-30892 may be administered one or more, preferably three, doses daily). An effective amount of *L. bulgaricus* B-30892 contained in the medicament is in a range from about $1 \times 10^5$ to about $1 \times 10^{12}$ colony forming units (CFU) of *L. bulgaricus* B-30892 per day and/or supernatant resulting from culturing about $1 \times 10^5$ to about $1 \times 10^{12}$ colony forming units (CFU) of *L. bulgaricus* B-30892 per day.

PepF belongs to the M3 metalloprotease family. While most bacterial PepFs are cytoplasmic endopeptidases, some are secreted; for example, the enzyme from *Bacillus amyloliquefaciens*. PepF has been seen in a variety of bacterial genuses including, *Lactococcus* and *Bacillus* and in *Bacillus subtilis*. In accordance with one or more embodiments, a medicament comprised of an effective amount of a non-pathogenic microorganism and/or its spores (that are capable of providing PepF) is administered to a patient to treat/cure GERD. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gas seri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), *Campylobacter subtilisis*, and *Oenococcus oeni* and their various strains. An effective amount of the microorganism and/or its spores is an amount that is effective to cause destruction or deactivation of neurological and/or muscular agents, mimics, immunogens and/or antigens that cause or exacerbate GERD. In accordance with one or more such embodiments, an effective amount is from about 100 thousand CFU to about 600 billion CFU per dose, where the dose is administered about one or more times per week, or as often as about one to about three times daily.

In accordance with one or more embodiments, a medicament comprised of an effective amount of parts of, or entirely broken up, microorganisms and/or their spores (that are capable of providing PepF) is administered to a patient to treat/cure GERD. Parts of the microorganisms and/or spores can be separated and selected, using any one of a number of methods that are well known to those of ordinary skill in the art, for their bioactive properties to help ensure and improve the rate of the destruction or deactivation of neurological agents, muscular agents, mimics, immunogens and/or antigens that cause or exacerbate GERD and/or to improve the effectiveness of enzymes in the gastrointestinal or respiratory tract in destroying or deactivating such mimics, immunogens and/or antigens. In accordance with one or more such embodiments, the microorganism and spores include, for example and without limitation, one or more of *Lactobacillus jensenii, Lactobacillus crispatus, Lactobacillus johnsonii, Lactobacillus plantarum, Lactobacillus helveticus, Lactobacillus amylolyticus, Lactobacillus salivarius, Lactobacillus ultunensis, Lactobacillus rhamnosus, Lactobacillus acidophilus, Lactobacillus delbrueki bulgaricus, Lactobacillus gasseri, Lactobacillus casei, Lactobacillus coleohominis, Lactobacillus fermentum, Lactobacillus paracasei, Lactococcus lactis cremoris, Enterococcus faecalis, Bacillus cereus* (spore-forming), and *Oenococcus oeni* and their various strains. An effective amount of the parts of, or entirely broken up, microorganisms and/or their spores is an amount sufficient to cause destruction or deactivation of neurological and/or muscular agents, mimics, immunogens and/or antigens that cause or exacerbate GERD. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more embodiments, an effective amount of endopeptidase O (PepO) administered will depend upon the severity of the disease process (the PepO may be administered in one or more, and preferably three, doses daily). However, an effective amount is in a range from about 20 units/day to about 200 units/day, where the definition of a unit is an amount of PepO required to cleave one micromole of bradykinin at a pH of 6.0 and a temperature of 25° C.

In accordance with one or more embodiments, an effective amount of PepO, in combination with the B-30892 strain, will be administered, and the amount will depend upon the severity of the disease process (the PepO and B-30892 may be administered one or more, preferably three, doses daily). An effective amount of *L. bulgaricus* B-30892 contained in the medicament is in a range from about $1 \times 10^5$ to about $1 \times 10^{12}$ colony forming units (CFU) of *L. bulgaricus* B-30892 per day and/or supernatant resulting from culturing about $1 \times 10^5$ to about $1 \times 10^{12}$ colony forming units (CFU) of *L. bulgaricus* B-30892 per day.

In accordance with one or more embodiments, a medicament comprised of an effective amount of a non-pathenogenic microorganism and/or its spores (that are capable of providing PepO) is administered to a patient to prevent/treat/cure GERD. PepO is found in a large range of bacterial systems. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antrii, Lactobacillus paracasei, Lactobacillus ruminis, Lactococcus lactis, Bifidobacterium dentium, Bifidobacterium longum, Bifidobacterium adolescentis, Bifidobacterium animalis*, and *Oenicoccus oeni* and their various strains. An effective amount of the microorganism and/or its spores is an amount that is effective to cause destruction or deactivation of neurological and/or muscular agents, mimics, immunogens and/or antigens that cause or exacerbate GERD. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entirely broken up, microorganisms and/or their spores (that are capable of providing PepO) is administered to a patient to prevent/treat/cure GERD. Parts of the microorganisms and/or spores can be separated and selected, using any one of a number of methods that are well known to those of ordinary skill in the art, for their bioactive properties to help ensure and improve the rate of the destruction or deactivation of neurological and/or muscular agents, mimics, immunogens or immunogens that cause or exacerbate GERD and/or to improve the effectiveness of enzymes in the gastrointestinal or respiratory tract in destroying or deactivating such neurological agents, mimics, immunogens and/or antigens. In accordance with one or more such embodiments, the microorganism and spores include, for example and without limitation, *Lactobacillus sanfrancisens, Lactobacillus plantarum, Lactobacillus acidophilus, Lactobacillus helveticus, Lactobacillus casei, Lactobacillus reuteri, Lactobacillus salivarius, Lactobacillus gasseri, Lactobacillus rhamnosus, Lactobacillus johnsonii, Lactobacillus jensenii, Lactobacillus amylolyticus, Lactobacillus sakei, Lactobacillus antri, Lactobacillus paracasei, Lactobacillus ruminis, Lactococcus lactis, Bifidobacterium dentium, Bifidobacterium longum, Bifidobacterium adolescentis, Bifidobacterium animalis*, and *Oenicoccus oeni* and their various strains. An effective amount of the parts of, or entirely broken up, microorganisms and/or their spores is an amount sufficient to cause destruction or deactivation of neurological and/or muscular agents, mimics, immunogens and/or antigens that cause or exacerbate GERD. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more further embodiments, a medicament comprised of an effective dose of endopeptidase O2 (PepO2) from *Bifidobacterium animalis* subsp lactis is administered to a patient to prevent/treat/cure GERD. Such PepO2 will destroy potential neurological and/or muscular agents, mimics, immunogens and/or antigens prior to immune activation.

In accordance with one or more embodiments, an effective amount of endopeptidase O2 (PepO2) administered will depend upon the severity of the disease process (the PepO2 may be administered in one or more, and preferably three, doses daily). However, an effective amount is in a range from about 20 units/day to about 200 units/day, where the definition of a unit is an amount of PepO2 required to cleave one micromole of BCN (f193-209) at a pH of 6.5 and a temperature of 25° C.

In accordance with one or more embodiments, an effective amount of PepO2, in combination with the B-30892 strain, will be administered, and the amount will depend upon the severity of the disease process (the PepO2 and B-30892 may be administered in one or more, preferably three, doses daily). An effective amount of *L. bulgaricus* B-30892 contained in the medicament is in a range from about $1\times10^5$ to about $1\times10^{12}$ colony forming units (CFU) of *L. bulgaricus* B-30892 per day and/or supernatant resulting from culturing about $1\times10^5$ to about $1\times10^{12}$ colony forming units (CFU) of *L. bulgaricus* B-30892 per day.

In accordance with one or more embodiments, a medicament comprised of an effective amount of a non-pathogenic microorganism and/or its spores (that are capable of providing PepO2) is administered to a patient to treat/cure GERD. In accordance with one or more such embodiments, the microorganism and spores include, for example and without limitation, *Lactococcus lactis cremoris, Lactobacillus helveticus*, and *Lactobacillus johnsonii* and their various strains. An effective amount of the microorganism and/or its spores is an amount that is effective to cause destruction or deactivation of neurological and/or muscular agents, mimics, immunogens and/or antigens that cause or exacerbate GERD. In accordance with one or more such embodiments, an effective amount is from about 100 thousand CFU to about 600 billion CFU per dose, where the dose is administered about one or more times per week, or as often as about one to three times daily.

In accordance with one or more embodiments, a medicament comprised of an effective amount of parts of, or entirely broken up, microorganisms and/or their spores (that are capable of providing PepO2) is administered to a patient to treat/cure GERD. Parts of the microorganisms and/or spores can be separated and selected, using any one of a number of methods that are well known to those of ordinary skill in the art, for their bioactive properties to help ensure and improve the rate of the destruction or deactivation of mimics, immunogens or immunogens that cause or exacerbate GERD and/or to improve the effectiveness of enzymes in the gastrointestinal or respiratory tract in destroying or deactivating such neurological and/or muscular agents, mimics, immunogens and/or antigens. In accordance with one or more such embodiments, the microorganism and spores include, for example and without limitation, *Lactococcus lactis cremoris, Lactobacillus helveticus*, and *Lactobacillus johnsonii* and their various strains. An effective amount of the parts of, or entirely broken up, microorganisms and/or their spores is an amount sufficient to cause destruction or deactivation of neurological and/or muscular agents, mimics, immunogens and/or antigens that cause or exacerbate GERD. In accordance with one or more such embodiments, an effective amount of parts or entirely broken up microorganisms is from about 100 thousand CFU to about 600 billion CFU per dose, where the dose is administered about one or more times per week, or as often as about one to three times daily. Methods for breaking up suitable microorganisms and/or spores include, for example and without limitation, sonication, crushing, shearing, oxidation, exposure to photonic radiation or chemical (for example, not limited to, enzymic) cleavage of the microorganisms.

In accordance with one or more embodiments, an effective amount of subtilisin administered will depend upon the severity of the disease process (the subtilisin may be administered in one or more, preferably three, doses daily). However, an effective amount is in a range from about 2,000 fibrinolytic units/day to about 10,000 fibrinolytic units/day. In accordance with one or more further embodiments, a medicament comprised of an effective amount of a non-pathogenic microorganism and/or its spore that are capable of providing subtilisin is administered to a patient to treat/cure GERD.

In accordance with one or more embodiments, an effective amount of subtilisin, in combination with the B-30892 strain, will be administered, and the amount will depend upon the severity of the disease process (the subtilisin and B-30892 may be administered in one or more, preferably three, doses daily). An effective amount of *L. bulgaricus* B-30892 contained in the medicament is in a range from about $1\times10^5$ to about $1\times10^{12}$ colony forming units (CFU) of *L. bulgaricus* B-30892 per day and/or supernatant resulting from culturing about $1\times10^5$ to about $1\times10^{12}$ colony forming units (CFU) of *L. bulgaricus* B-30892 per day.

In accordance with one or more such embodiments, suitable microorganisms and spores include, for example, but not limited to, *Bacillus subtilis, Bacillus licheniformis*, and *Bacillus lentus* and their various strains. An effective amount of the microorganism and/or its spores is an amount that is effective to cause destruction or deactivation of neurological and/or muscular agents, mimics, immunogens and/or antigens that cause or exacerbate GERD. In accordance with one or more such embodiments, an effective amount is from about 100 thousand CFU to about 600 billion CFU per dose (CFU designates colony forming units), where the dose is administered about one or more times per week, or as often as about one to about three times daily. In accordance with one or more still further embodiments, a medicament comprised of an effective amount of parts of, or entirely broken up, microorganisms and/or their spores capable of providing subtilisin, is administered to a patient to prevent/treat/cure GERD. Parts of the microorganisms and/or spores can be separated and selected, using any one of a number of methods that are well known to those of ordinary skill in the art, for their bioactive properties to help ensure and improve the rate of the destruction or deactivation of neurological and/or muscular agents, mimics, immunogens or immunogens that cause or exacerbate GERD and/or to improve the effectiveness of enzymes in the gastrointestinal or respiratory tract in destroying or deactivating such neurological and/or muscular agents, mimics, immunogens and/or antigens.

In accordance with one or more embodiments, the above-described medicaments can be administered or delivered orally or via the nose or by suppository or by injection into a patient's gut (for example, and without limitation, by enema, endoscope, colonoscope, robotically actuated capsule, and so forth), to act as a prophylactic in the upper respiratory and/or gastrointestinal tract to prevent/treat/cure GERD. As used herein, oral delivery includes, for example and without limitation, a capsule; a tablet; a chewable tablet/capsule; a spray; a gel, a liquid drink, a food, a powder, a gum, a candy, or cream containing the product. The term orally delivery includes sublingually, and on an absorbent substrate or adsorbent substrate. In accordance with one or more embodiments, a medicament can be administered rectally, where a rectal delivery mechanism includes, for example and without limitation, an enema, a fecal transplant, a gel, a cream, an ointment, or a suppository. A fecal transplant includes at least some of the following. First, a donor of feces is screened to look for parasites, pathogenic microorganisms, and to measure the kinds of microbes that are in the donor's feces. The donor's feces are also analyzed for chemicals having, for example, but not limited to, proteolytic activity. Next, the microbial and chemical measurements are compared against a set of requirements for a successful transplant, for example, but not limited to, the presence of bacteria or chemical activity that can destroy neurological agents, mimics, immunogens and/or antigens that cause or exacerbate GERD. Next, the donor's feces may be corrected for pH level by adding acids, bases, or appropriate buffering agents. Any imbalance of enzymes may be corrected by selecting an appropriate enzyme or pro- or co-enzyme producing microbe. A candidate microbe may be identified in the manner described below. Next, undesirable bacteria can be neutralized or killed. If the donor's feces do not have sufficient ability to destroy neurological and/or muscular agents, mimics, immunogens and/or antigens that cause or exacerbate GERD, then microorganisms that are capable of destroying neurological and/or muscular agents, mimics, immunogens and/or antigens that cause or exacerbate GERD, are added, in an effective amount, to the donor's feces prior to a fecal enema or around the time of the fecal enema to populate the sick person's gastrointestinal tract.

In accordance with one or more embodiments, the above-described medicaments can be administered transdermaly, where a transdermal delivery mechanism includes, for example and without limitation, a skin patch, a spray, a gel, a cream, an ointment or a bath. In accordance with one or more embodiments, the above-described medicaments can be administered intravenously, where intravenous delivery includes, for example and without limitation, injection of the medicament mixed into an intravenous solution. In accordance with one or more embodiments, the above-described medicaments can be administered by inhalation, where intravenous delivery includes, for example and without limitation, a nebulized powder inhaled by the nose or mouth.

In accordance with one or more such embodiments, treatment may range from about weekly to about daily, and be ongoing until symptoms of GERD have disappeared.

The following describes methods for preparing useful microorganisms. Fermentation: As an example, microorganism *Bacillus subtilis* Natto produces the endoprotease subtilisin. Fermentation additives may be added to a culture of the microorganisms to enhance: production of microorganisms, ability of the microorganisms to survive in the gastrointestinal tract, ability of the microorganisms to adhere to the gastrointestinal tract, ability of the microorganisms to secrete desired proteases, ability of the microorganisms to secrete chemicals to enhance survival of proteases, ability of the microorganisms to secrete chemicals to enhance effectiveness of desired proteases, and ability of the microorganisms to secrete chemicals to interfere with undesired chemicals. Also, the amount and kinds of sugars, vitamins, amino acids, proteins and/or fats available to the microorganisms, prior to drying and forming a powder, affect their viability. Examples of useful sugars are, but are not limited to, sucrose, fructose, glucose, lactose, trehalose, raffinose, palainose, lactulose, lactitol, xylitol, sorbitol, mannitol, malstose, dextrin and maltodextrin. Examples of useful antioxidants are, but are not limited to, ascorbic acid, glutathione and alpha-lipoic acid. Examples of useful amino acids or their salts are, but are not limited to, lysine, cysteine, glycine and glutamate. Examples of useful oils are, but are not limited to, butter, palm oil, nut oil, cocoa oil, rapeseed oil and soybean oil. Examples of useful stabilizing ingredients are, but are not limited to, soybean oligosaccharides, frutooligosaccharides, galactooligosaccharides, galactosyl lactose, milk, milk powders, whey, whey protein concentrates, casein, casein hydrolysates, lactoferrin, lactoperoxidase, lactoglobulins, glymacropeptides, lacto-saccharides, glycomacropeptides, lacto-saccharides and lacto-lipids. Examples of useful vitamins are, but are not limited to, vitamin D3 and vitamin E.

A chemical that inactivates an enzyme is, for example and without limitation, a serpin. Thus, it is desirable to inhibit serpins that inactivate proteases that destroy neurological agents and/or muscular, mimics, antigens, or immunogens that cause autoimmune disease. Also, protective agents such as, for example and without limitation, cryoprotectants or other chemicals such as gels, starches, polysaccharides, and/or sugars can be added to the culture to protect the microorganisms during the manufacturing processes.

Removing Liquid: When a powdered form of a microorganism is required, the microorganisms may need to have liquid removed. One option, known to those of ordinary skill in the art, is to centrifuge the fermentation mixture to reduce the amount of liquid. Other options include, but are not limited to, settling and membrane filtration. This concentrates the microbes by separating them from their supernatant. As such, it allows for more microbes per kilogram of dried product to keep transportation and storage costs down and to deliver more microbes per capsule or pill. It also allows the microbes to be added as a concentrated powder to be mixed into a drink or sprinkled onto food. Centrifuging is beneficial when the supernatant does not contain substantial amounts of bioactive substances that the microbes cannot readily secrete or create in the gastrointestinal tract. However, if the supernatant has the bioactive substances for therapeutic effect, then centrifuging does not need to be performed if the microbes are still desired. In some cases, centrifuging or other separation processes, known to those of ordinary skill in the art, may be desired to obtain the bioactive substances, such as enzymes or bacteriocins, for delivery without the microbe. The following methods may also be used to separate microorganisms from supernatant: sedimentation, ultrafiltration and reverse osmosis.

Drying: This step dries the microorganisms as well as any available supernatant. The microorganisms can be dried with freeze-drying techniques, known to those of ordinary skill in the art, by placing the centrifuged microbes and residual supernatant, which form a slurry, onto trays and freezing them in a vacuum environment. After the slurry dries, it resembles a cake. The dried cake is then crushed, and the crushed powders are sieved to obtain the desired particle size distribution. This process of drying in bulk followed by crushing often kills many bacteria due to the thermal and mechanical stresses applied to the microbes. Another method of making a powder, known by those of ordinary skill in the art, is to spray dry the microorganisms. For this process the slurry is sprayed through a nozzle into a heated air environment. The incoming slurry can be heated or unheated. If the shear forces and temperatures that the microorganisms and/or enzymes experience during the heated spray drying process are too great, microorganisms will die or be damaged enough that the intended therapeutic effectiveness of the microorganism and/or enzyme will be diminished. To improve the yield and prevent damage to surviving microorganisms, an electrospray drying process can be used. An example of a manufacturer who makes suitable electrospray drying equipment is ZoomEssence, Inc. at www.zoomessence.com.

Blending: Other ingredients, such as but not limited to, dried proteases, microorganisms, protective sugars, polysaccharides, gums, oils, desiccants, anti-oxidants, and bacteriocins, can be added prior to or after the drying process. These ingredients will assist the microbes in surviving during storage as well as in passing to the target areas of the gastrointestinal tract. Also adding other ingredients is needed to reduce the dosage of concentrated microbial powders to the dosages required for delivery to the person.

Delivery: A powder can also be an acceptable delivery system especially when microorganisms do not need to be alive and where either their microbial parts or their secreted bioactive substances are effective against pathogens or for normalizing protease ratios. The powder can be consumed by adding the powder to a food or drink product. The powder containing the microorganisms, and/or supernatant, and/or enzymes can be formulated by those of ordinary skill in the art into a drink that may contain for example, but not limited to, water, sweeteners, flavorings, colorants, anti-oxidants, vitamins, minerals, short-chain fatty acids, stimulants, mood-enhancers, teas, anti-inflammatories, and other bioactive ingredients. The powder can be consumed after sprinkling or pouring it over solid food or mixing into a liquid. The powder can be packaged into bulk containers such as a bag or can or into individual sachets for easy of carrying and single use dosing. To form a tablet, a powder containing the microbes and/or enzyme(s), excipients, and/or other bioactive substances are compressed into a mold in a tableting machine. The tablet can be coated with methods and processes known to those of ordinary skill in the art to prevent the premature dissolution of the product in the stomach to keep the microbes alive for delivery further down the gastrointestinal (GI) tract. Such coatings are designed by those of ordinary skill in the art to dissolve by time in the GI tract or more preferably by pH exposure as the pH along the GI tract is acidic in the stomach and the pH increases by the time the digested contents reach the large intestine. At the large intestine, the pH is approximately 7. Some examples known to those of ordinary skill in the art of a pH triggered coating are, but not limited to, Eudragit and shellac. The tablet can be designed by those of ordinary skill in the art to be consumed orally or inserted into the rectum as a suppository. To form a capsule, a powder containing the microorganisms, supernatant, enzymes, excipients and/or other bioactive substances are directed into a capsule that can be made of materials known to those of ordinary skill in the art, but are not limited to, hardened gelatin or other polymer. The capsule can be coated by processes known to those of ordinary skill in the art to prevent the premature dissolution of the product in the stomach to keep the microorganisms alive and enzymes effective for delivery further down the GI tract. Such coatings known to those who are of ordinary skill in the art are designed to dissolve by time in the GI tract or more preferably by pH exposure. Some examples known to those of ordinary skill in the art of a pH triggered coating are, but not limited to, Eudragit and shellac. The capsule can be designed by those of ordinary skill in the art to be consumed orally or inserted into the rectum as a suppository. An alternate form of a capsule to contain the microorganisms, enzymes, excipients, and/or other bioactive substances is a gel capsule that can be made of materials and processes known to those of ordinary skill in the art.

For a liquid delivery system, the microorganisms and/or supernatant and/or enzymes and bioactive substances can be introduced in a fermented liquid. That liquid can be in the form of cultured or non-cultured animal-based and/or plant-based milk such as, but not limited to, cow's, goat's, rice, almond, and/or soymilk. Alternatively, microorganisms and/or enzymes can added to a drink such, as but not limited to, a juice or formulated into a drink that may contain for example but not limited to water, sweeteners, flavorings, colorants, anti-oxidants, vitamins, minerals, short-chain fatty acids, stimulants, mood-enhancers, teas, anti-inflammatories and other bioactive ingredients. For a solid delivery system the microorganisms and/or enzymes and bioactive substances can be added to solid food in accordance with a number of methods that are well known to those of ordinary skill in the art. Examples of such food are, but are not limited to, candy, confectionary, chewing gum, energy bars, fermented/dried vegetables, fermented/dried meat, fermented/dried seafood, fermented/dried fruit, fermented/dried beans and frozen desserts. For a slurry delivery system the microorganisms and/or enzymes and bioactive substances can be added to slurry foods in accordance with a number of methods that are well known to those of ordinary skill in the art. Examples of such food are, but not limited to, yogurt, jams, jellies, gravies, gel shots, puddings, frozen desserts, salad dressings, syrups and spreads.

Embodiments of the present invention described above are exemplary, and many changes and modifications may be made to the description set forth above by those of ordinary skill in the art while remaining within the scope of the invention. As such, the scope of the invention should be determined with reference to the appended claims along with their full scope of equivalents.

What is claimed is:

1. A method of mitigating or treating Gastroesophageal Reflux Disease (GERD) caused by a neurological disorder comprises:
   administering an effective amount of a medicament comprised of *Lactobacillus bulgaricus* B-30892 to a human to mitigate or treat GERD caused by a neurological disorder.

2. The method of claim 1 wherein the medicament further comprises oligopeptidase F (PepF).

3. The method of claim 1 wherein the medicament further comprises endopeptidase O (PepO).

4. The method of claim 1 wherein the medicament further comprises endopeptidase O2 (PepO2).

5. The method of claim 1 wherein the medicament further comprises subtilisin.

* * * * *